(12) United States Patent
Zhou et al.

(10) Patent No.: US 12,099,051 B2
(45) Date of Patent: Sep. 24, 2024

(54) METHOD FOR ESTABLISHING BIOLOGICAL MODEL ON JOINT TOXICITY OF CAENORHABDITIS ELEGANS AND APPLICATION THEREOF

(71) Applicant: SOUTHWEST UNIVERSITY, Chongqing (CN)

(72) Inventors: Hongyuan Zhou, Chongqing (CN); Liang Ma, Chongqing (CN); Yuhao Zhang, Chongqing (CN)

(73) Assignee: SOUTHWEST UNIVERSITY, Chongqing (CN)

( * ) Notice: Subject to any disclaimer, the term of this patent is extended or adjusted under 35 U.S.C. 154(b) by 0 days.

(21) Appl. No.: 18/371,493

(22) Filed: Sep. 22, 2023

(65) Prior Publication Data

US 2024/0118264 A1    Apr. 11, 2024

(30) Foreign Application Priority Data

Sep. 22, 2022   (CN) .......................... 202211160979.X

(51) Int. Cl.
| | | |
|---|---|---|
| *G01N 33/00* | (2006.01) | |
| *G01N 1/34* | (2006.01) | |
| *G01N 33/50* | (2006.01) | |

(52) U.S. Cl.
CPC ........... *G01N 33/5014* (2013.01); *G01N 1/34* (2013.01); *G01N 33/5085* (2013.01); *G01N 2333/43534* (2013.01); *G01N 2500/10* (2013.01)

(58) Field of Classification Search
None
See application file for complete search history.

(56) References Cited

U.S. PATENT DOCUMENTS

2011/0092578 A1* 4/2011 Monte ................. A61K 36/185
568/45

OTHER PUBLICATIONS

Kumari (Nature, 2021, scientific reports, vol. 11, 19420, 1-14) (Year: 2021).*
Khanna (Arch. Environ. Contam. Toxicol. 32, pp. 110-114) (Year: 1997).*
Hanna (Environ. Scil: Nano, 2016, vol. 3, 1080-1089). (Year: 2016).*
Mengzhou Zhou, et al., The use of Caenorhabditis elegans model to screen lactobacilli for the control of patulin, Food Control, 2022, pp. 1-9, vol. 137, 108963.

* cited by examiner

*Primary Examiner* — Celine X Qian
(74) *Attorney, Agent, or Firm* — Bayramoglu Law Offices LLC

(57) ABSTRACT

A method for establishing a biological model on joint toxicity of *Caenorhabditis elegans* and an application thereof are provided. The method for establishing the biological model includes adding the L1-stage *Caenorhabditis elegans* to a mixed system of working solution of mycotoxins containing tenuazonic acid and penicillin, K-medium solution and *E. coli* OP50 to obtain L1-stage *Caenorhabditis elegans*. The biological model indicates that TeA and PAT have a synergistic effect on the growth, development and reproductive ability of *Caenorhabditis elegans*, and their toxicity mechanism is related to inducing nematodes and stimulating transcriptional factors of Daf-16 genes. The biological model and detection method are simple to operate and its test period is short.

5 Claims, 7 Drawing Sheets

METHOD FOR ESTABLISHING BIOLOGICAL MODEL ON JOINT TOXICITY OF CAENORHABDITIS ELEGANS AND APPLICATION THEREOF

CROSS REFERENCE TO THE RELATED APPLICATIONS

This application is based upon and claims priority to Chinese Patent Application No. 202211160979.X, filed on Sep. 22, 2022, the entire contents of which are incorporated herein by reference.

TECHNICAL FIELD

The present invention relates to the technical field of establishing biological models, in particular to a method for establishing a biological model on joint toxicity of *Caenorhabditis elegans* and an application thereof.

BACKGROUND

Tenuazonic acid (TeA) is an emerging mycotoxin with acute toxicity that can cause gastrointestinal bleeding and other problems, often found in wheat, tomatoes, citrus and other grains, fruits and vegetables. Patulin (PAT) widely exists in fruits and products, and it can cause gastrointestinal disorders. TeA and PAT tend to coexist in fruits, and both can impair gastrointestinal function.

Animal models are currently the most effective experimental models for evaluating toxicity, metabolism and toxicity mechanisms. Commonly-used animal models include mice, rats, fruit flies, broilers, rabbits, etc., although such large animals have high homology with humans, but for them the experimental requirements are strict, the experimental processes are inconvenient, time-consuming, costly, and easy to cause ethical issues.

SUMMARY

Based on this, it is necessary to provide a method for establishing a biological model on joint toxicity of *Caenorhabditis elegans* and an application thereof, which have a short experimental period, low costs, easy to operate, and used to quantitatively study the toxicity mechanism of mycotoxin joint contamination.

The present invention adopts the following technical solution.

The present invention provides a method for establishing a biological model on joint toxicity of *Caenorhabditis elegans*, including the steps of: obtaining L1-stage *Caenorhabditis elegans*; adding the L1-stage *Caenorhabditis elegans* to a mixed system of working solution of mycotoxins containing tenuazonic acid and penicillin, K-medium solution and *E. coli* OP50, then incubating the mixed system in a biological incubator for at least 24 h to obtain a joint toxic biological model of *Caenorhabditis elegans*.

In some examples, the mixed system contains 50 μL *E. coli* OP50 and 30 μL L1-stage *Caenorhabditis elegans* (about 80~100), the concentration ratio of the tenuazonic acid to the penicillin is 1:1, and the concentration of the tenuazonic acid is at least 2.5 μg/mL, and the concentration of the penicillin is at least 2.5 μg/mL.

In some examples, the *Caenorhabditis elegans* is selected from at least one of a wild type N2, a mutant strain Daf-16 (mu86), and a mutant strain Daf-2 (e1370). Preferably, the *Caenorhabditis elegans* is selected from the mutant strain Daf-16 (mu86).

In some examples, the step of obtaining L1-stage *Caenorhabditis elegans* includes: adding an appropriate amount of K-medium solution to a NGM medium containing a large number of gestational nematodes, then scraping out the nematodes and eggs with an L-shaped coating rod, then pipetting them into a centrifuge tube by means of a Pasteur pipette, next centrifugating them to remove the supernatant; adding lysis solution to the centrifuge tube for lysis, then centrifugating them to remove the supernatant; then washing them several times with K solution, next suctioning the eggs into a perforated plate, finally incubating them in a biochemical incubator to obtain synchronized L1-stage nematodes.

In some examples, the lysis solution is an aqueous solution containing 10 g/L NaOH and 6.5% NaClO.

In some examples, the method for establishing a biological model on joint toxicity of *Caenorhabditis elegans* further includes the step of verifying the growth and reproductive capacity of *Caenorhabditis elegans*.

A biological model on joint toxicity of *Caenorhabditis elegans* is established through the above method.

The present invention further provides an application of Daf-16 genes in studying the regulating effect of mycotoxin toxicity.

An application of the above method for establishing a biological model on joint toxicity of *Caenorhabditis elegans* in the screening of anti-mycotoxin drugs.

Compared with the prior art, the present invention has the following the beneficial effects.

The present invention uses TeA and PAT to jointly contaminate *Caenorhabditis elegans* to establish a biological model on toxicity, indicating that TeA and PAT have a synergistic effect on the growth, development and reproductive ability of *Caenorhabditis elegans*, and their toxicity mechanism is related to inducing nematodes and stimulating transcriptional factors of Daf-16 genes. The present invention provides a test basis for the formulation of the safety limit of TeA and PAT in food, and the adopted biological model and detection method are simple to operate, its test period is short, making it possible that researchers can quickly study the joint toxic effect of toxic substances and its mechanism.

BRIEF DESCRIPTION OF THE DRAWINGS

FIGS. 1A-1C are statistical charts showing the effects on the growth and development of *Caenorhabditis elegans* after separately exposing the TeA and PAT for 24 h, 48 h and 72 h and jointly exposing them for 24 h and 48 h in Example 2.

FIGS. 2A-2C are statistical charts showing the effects on the reproductive capacity of *Caenorhabditis elegans* after separately and jointly exposing the TeA and PAT in Example 3.

FIG. 3 is a statistical chart showing the effects of separately and jointly exposing the TeA and PAT on oxidative stress of *Caenorhabditis elegans* in Example 4.

FIGS. 4A-4C are statistical charts showing the effects of TeA, PAT, TeA+PAT on the growth and development of mutant strains in Example 5.

FIGS. 5A-5C are statistical charts showing the effects of TeA, PAT, TeA+PAT on the reproductive ability of mutant strains in Example 5.

DETAILED DESCRIPTION OF THE EMBODIMENTS

Figure 1A:
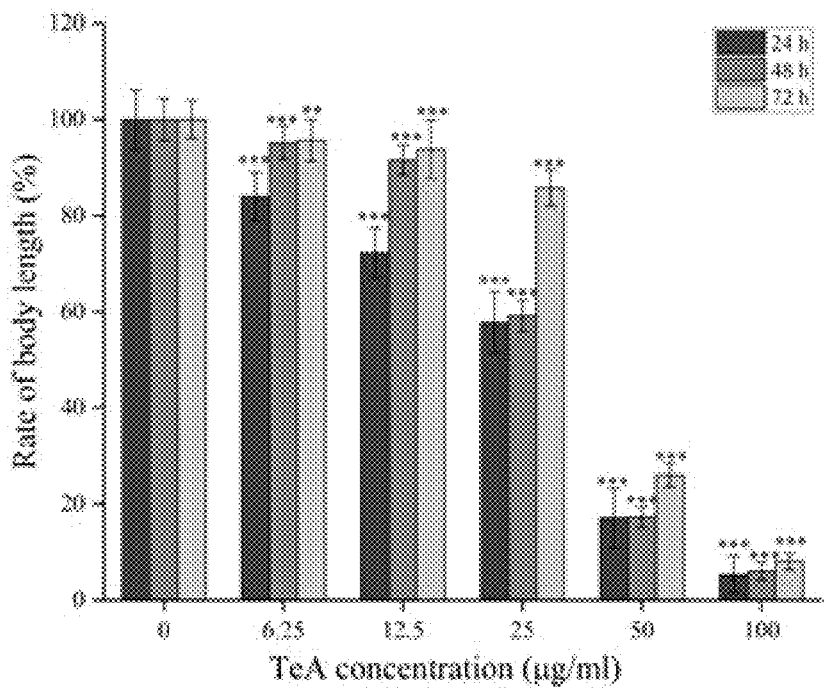

The present invention is further described in combination with specific examples, so that a person skilled in the art can understand the present invention more clearly.

The following examples is only used to explain the present invention, but not to limit the scope of the present invention. Based on specific examples in the present invention, all other embodiments obtained by a person skilled in the art without doing creative work fall within the protection scope of the present invention.

In the examples of the present invention, unless otherwise specified, all raw material ingredients are commercially available products well known to a person skilled in the art; in the examples of the present invention, if not specified, the adopted technical means are conventional means well known to a person skilled in the art.

The *Caenorhabditis elegans* of the wild-type N2 or the mutant strains Daf-16 (mu86) and Daf-2 (e1370) is selected as biological test materials and purchased from the *Caenorhabditis* Genetics Center (CGC).

Preparing K-medium solution: adding 3.54 g KCl and 4.50 g NaCl to a 2 L flask, adding 1500 mL ultrapure water to dissolve them, sterilizing at 121° C. for 30 min, then obtaining K-medium solution.

Preparing NGM medium: adding 1.77 g KCl, 2.25NaCl, 14.5 g agar and 3.76 g tryptone to a 2 L flask, adding 750 mL ultrapure water to mix them well, sterilizing at 121° C. for 30 min, taking out the mixed solution and cooling it to 70° C., adding 1 mL of 1M $CaCl_2$ (11.1 g/100 mL ultrapure water, sterilized), 1 mL of 1M $MgSO_4$ (24.7 g/100 mL ultrapure water, sterilized), 1 mL cholesterol (1 g/100 mL absolute ethanol, heated and dissolved), after mixing well, quickly pouring the mixed solution into a 9 cm culture dish in an ultra-clean table, resting under cooling UV irradiation overnight to obtain NGM medium.

Preparing NGM containing *E. coli* OP50: adding 100 μL *E. coli* OP50 to the surface of NGM medium, after evenly coating it by using an L-shaped coating rod, incubating upside-down at 37° C. for 48 h in a biochemical incubator to obtain NGM containing *E. coli* OP50, then storing it at 4° C.

Preparing TeA mother liquor: dissolving 20 mg TeA in 1 mL dimethyl sulfoxide (DMSO) to obtain 20 mg/mL TeA mother liquor, storing it at −20° C., melting it at room temperature before use.

Preparing PAT mother liquor: dissolving 10 mg PAT in 1 mL dimethyl sulfoxide (DMSO) to obtain 10 mg/mL PAT mother liquor, storing it at −20° C., melting it at room temperature before use.

Diluting the TeA mother liquor with K-medium to obtain 200 μg/mL TeA working solution.

Diluting the PAT mother liquor with K-medium to obtain 100 μg/mL PAT working solution.

Examples are as follows:

Example 1

The method for obtaining synchronized L1-stage *Caenorhabditis elegans* provided by this example includes the steps of adding an appropriate amount of K-medium solution to a NGM medium containing a large number of gestational nematodes, then scraping out the nematodes and eggs with an L-shaped coating rod, then pipetting them into a 15 mL centrifuge tube by means of a Pasteur pipette, next centrifugating them to remove the supernatant; adding 10 mL lysis solution (1 g NaOH+20 mL 6.5% NaClO+80 mL ultrapure water) to the centrifuge tube for lysis, after full lysis, centrifugating them to remove the supernatant; then washing them 3 times with K solution, next suctioning the eggs into a 12-hole culture plate, finally incubating them in a biochemical incubator at 20° C. for 10 h to obtain L1-stage nematodes.

Having obtained synchronized L1-stage *Caenorhabditis elegans* in this example ensures that the nematodes used in subsequent experiments are in a uniform growth state.

Example 2

The method for establishing a biological model on joint toxicity of *Caenorhabditis elegans* provided by this example includes the following steps.

S1. Diluting the synchronized L1-stage *Caenorhabditis elegans* obtained in Example 1 to 80~100/30 μL. Adding 920 μL medium, different groups of toxin working solution, 30 μL diluted L1 nematodes and 50 μL OP50 sequentially into the 12-hole culture plate, incubating 3 groups per concentration in parallel at 20° C. in a biological incubator.

The different groups of toxin working solution are as follows:

The experimental doses of TeA include 0, 6.25, 12.5, 25, 50, 100 μg/mL.

The experimental doses of PAT include 0, 5, 25, 50 μg/mL.

The jointly-exposed doses of TeA and PAT are 0, 2.5, 12.5, and 25 μg/mL, respectively.

S2. Suctioning *Caenorhabditis elegans* exposed for 24 h, 48 h, and 72 h respectively into an evaporation dish, fixing the nematodes with 10% formalin solution, placing the dish at bottom of the fluorescence upright microscope to photograph and measure the body length of nematodes by means of Image view software, keeping no less than 20 nematodes in each experimental concentration group.

S3. Processing data: performing significance analysis on all data by using SPSS 24.0 software, representing results as mean t standard deviation, plotting by using origin 2021, representing significance levels as *($P<0.05$), ($P<0.01$) and *($P<0.001$). calculating the joint effect (CI) of TeA and PAT by using Compusyn software, wherein − stands for antagonism, + stands for synergy, and + stands for addition.

Figure 1B:
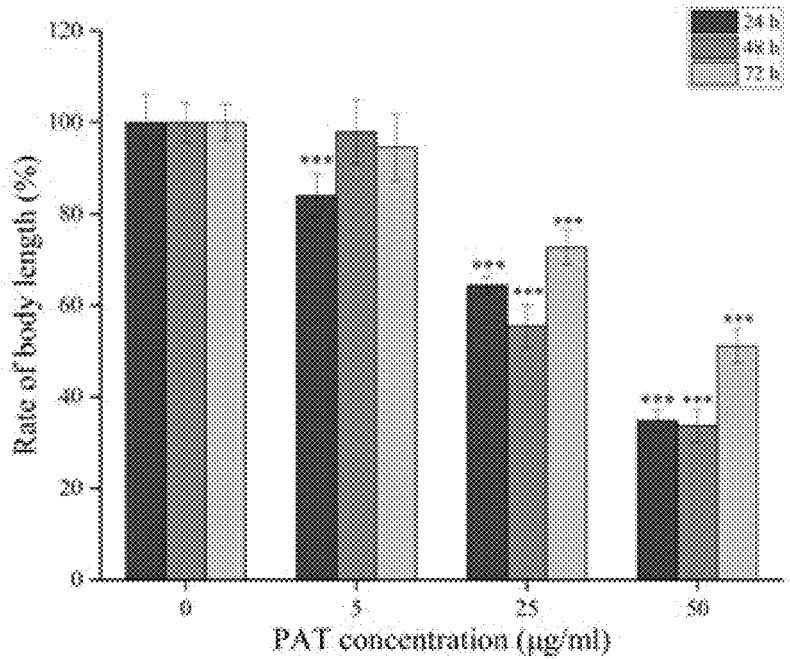
Figure 1C:
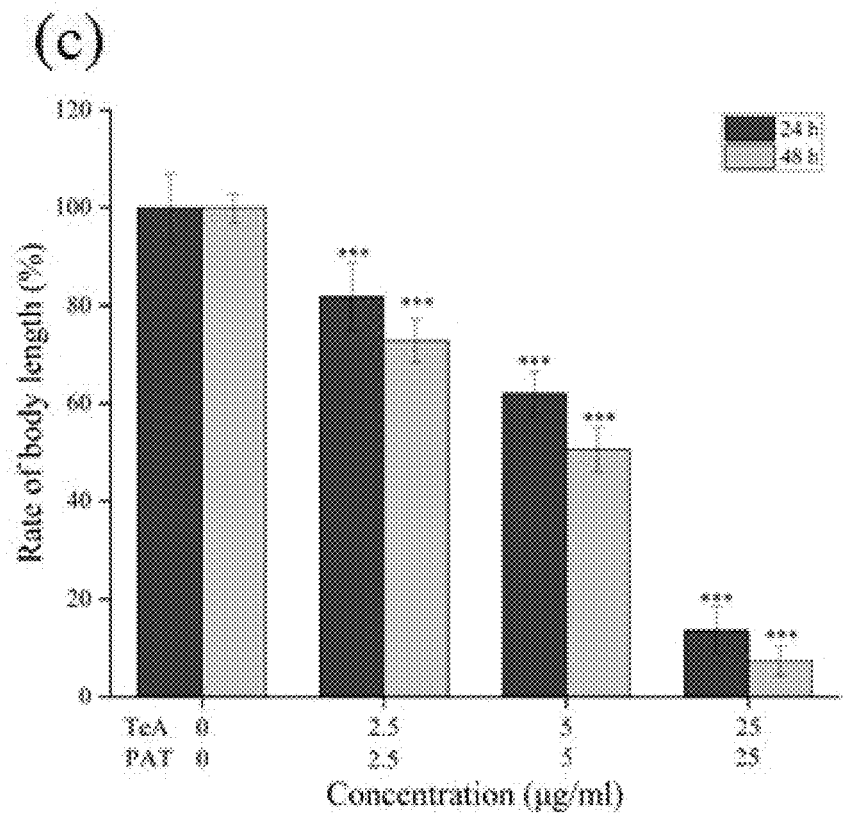
Figure 2A:
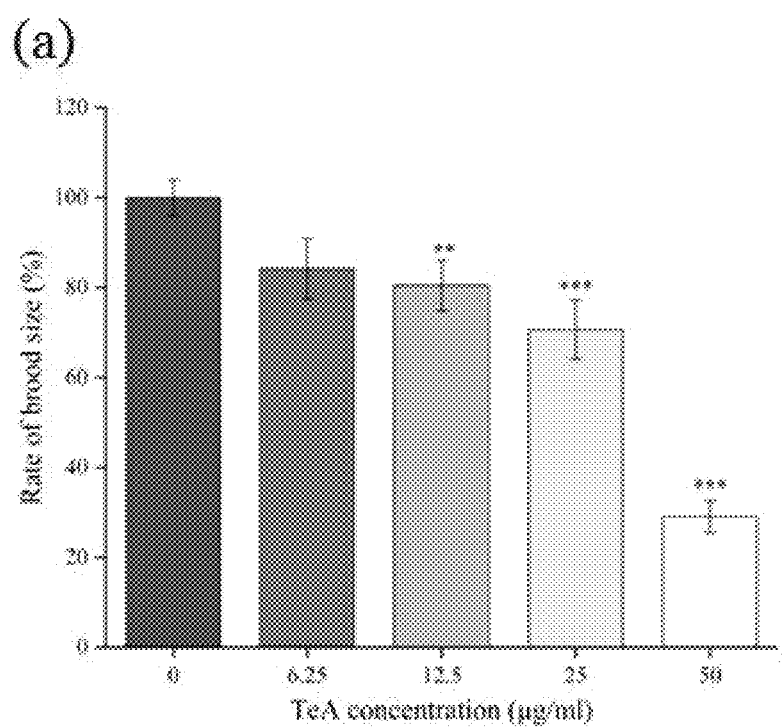
Figure 2B:
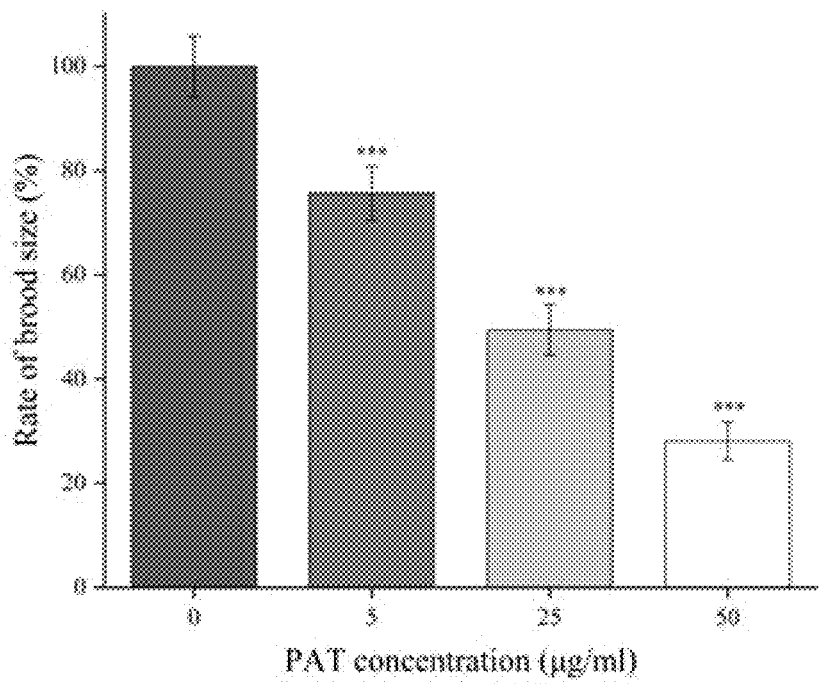
Figure 2C:
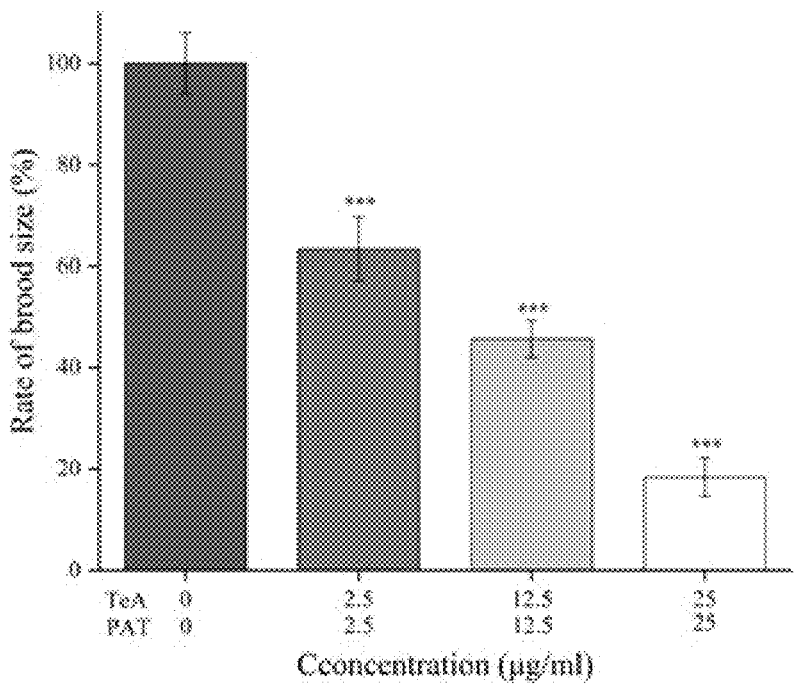

The statistical results are shown in FIGS. 1A-1C (showing the effects on the growth and development of *Caenorhabditis elegans* after separately exposing the TeA and PAT for 24 h, 48 h and 72 h and jointly exposing them for 24 h and 48 h), as well as in Table 1 and Table 2 as follows.

TABLE 1

$EC_{50}$ and joint effects on the growth and development of Caenorhabditis elegans after exposing for 24 h.

| mycotoxin | $EC_{50}$ | $EC_{10}$ | $EC_{25}$ | $EC_{75}$ | $EC_{90}$ |
|---|---|---|---|---|---|
| TeA | 32.42 μg/mL | | | | |
| PAT | 44.21 μg/mL | | | | |

TABLE 1-continued

EC$_{50}$ and joint effects on the growth and development of Caenorhabditis elegans after exposing for 24 h.

| mycotoxin | EC$_{50}$ | EC$_{10}$ | EC$_{25}$ | EC$_{75}$ | EC$_{90}$ |
|---|---|---|---|---|---|
| TeA + PAT | 19.14 µg/mL ++ | 3.56 µg/mL + | 8.26 µg/mL ++ | 44.37 µg/mL ++ | 102.82 µg/mL ++ |

TABLE 2

EC$_{50}$ and joint effects on the growth and development of Caenorhabditis elegans after exposing for 48 h

| mycotoxin | EC$_{50}$ | EC$_{10}$ | EC$_{25}$ | EC$_{75}$ | EC$_{90}$ |
|---|---|---|---|---|---|
| TeA | 38.30 µg/mL | | | | |
| PAT | 40.65 µg/mL | | | | |
| TeA + PAT | 12.70 µg/mL +++ | 2.53 µg/mL ++++ | 5.68 µg/mL +++ | 28.40 µg/mL +++ | 63.50 µg/mL ++ |

Compared with the blank group, the body length of N2 wild-type nematodes gradually decreases with the increase in the concentration of the TeA and PAT, indicating that both TeA and PAT had a concentration-dose effect on the growth and development of nematodes. The nematode's body length is significantly confined at TeA concentration of 12.5 µg/mL (P<0.001), while the nematode's body length is significantly confined at PAT concentration of 25 µg/mL (P<0.001), but the joint exposure of TeA and PAT significantly confines the nematode's body length (P<0.001) at only 2.5 µg/mL.

When the separate and joint concentrations both are 25 µg/mL, the body length ratios of TeA, PAT, and TeA+PAT are 57.80%, 64.45% and 86.35%, after exposure for 24 h, respectively, and the body length ratios are 59.16%, 55.55% and 92.64%, respectively, after 48 h exposure, showing that TeA and PAT have a synergistic effect on the growth and development of nematodes.

Table 1 and 2 show the EC$_{50}$ and joint effects on the growth and development of Caenorhabditis elegans after separately and jointly exposing the TeA and PAT for 24 h and 48 h, and Compusyn calculates that the TeA and PAT show a synergistic effect in the concentration range of EC$_{10}$~EC$_{90}$.

Example 3

The present example tries out the effect of joint toxicity on the reproductive capacity of Caenorhabditis elegans, and the test method includes the following steps:

Referring to Example 2 to establish a biological model on joint toxicity of Caenorhabditis elegans.

Suctioning the nematodes after separately and jointly exposing the TeA and PAT for 48 h into a 1.5 mL EP centrifuge tube, after natural lysis, suctioning the nematodes on the bottom onto OP50-free NGM medium by means of a glass Pasteur pipette, after natural air drying in an ultra-clean table, picking single nematode into a 12-hole culture plate in which each hole contains 970 µL K-medium solution, 30 µL OP50, and one nematode, incubating the nematodes at 20° C. for 72 h in a biochemical incubator, after incubation, suctioning the nematodes from each hole to a evaporation dish, then adding 10/formalin solution to fix the nematodes, counting the nematodes in each hole under a fluorescence upright microscope, making at least 6 test in parallel for the experimental group at each concentration. The data processing method is the same as Example 2.

The statistical results are shown in FIGS. 1A-1C (showing the effects on the reproductive capacity of Caenorhabditis elegans after separately and jointly exposing the TeA and PAT), as well as in Table 3 as follows.

TABLE 3

EC$_{50}$ and joint effects on the reproductive capacity of Caenorhabditis elegans after exposing for 48 h.

| mycotoxin | EC$_{50}$ | EC$_{10}$ | EC$_{25}$ | EC$_{75}$ | EC$_{90}$ |
|---|---|---|---|---|---|
| TeA | 33.20 µg/mL | | | | |
| PAT | 29.92 µg/mL | | | | |
| TeA + PAT | 11.61 µg/mL +++ | 0.76 µg/mL +++ | 2.99 µg/mL +++ | 45.16 µg/mL +++ | 175.59 µg/mL ++ |

Compared with the blank group, the body length of N2 wild-type nematodes gradually decreases with the increase in the concentration of the TeA and PAT, indicating that both TeA and PAT had a concentration-dose effect on the reproductive capacity of nematodes. The nematode's spawning rate is significantly confined at TeA concentration of 12.5 µg/mL (P<0.001), while the nematode's spawning rate is significantly confined at PAT concentration of 5 µg/mL (P<0.001), but jointly treating the nematode significantly at respective 2.5 µg/mL TeA and PAT will significantly confine its spawning rate (P<0.001). When the separate and joint concentrations are 25 µg/mL, the spawning rate of TeA, PAT and TeA+PAT are 70.63%, 49.41% and 18.37%, respectively, indicating that TeA and PAT have a synergistic effect on the reproductive ability of nematodes.

Table 3 shows the $EC_{50}$ and joint effects on the reproductive capacity of *Caenorhabditis elegans* after separately and jointly exposing the TeA and PAT, and Compusyn calculates that the TeA and PAT show a synergistic effect in the concentration range of $EC_{10}\sim EC_{90}$.

Example 4

The present example tests the effect of separate and joint exposure of TeA and PAT on oxidative stress of *Caenorhabditis elegans*, in order to eliminate the effect of variations in body type on reactive oxygen species (ROS), the toxic dose has appropriately decreased, and the experimental concentrations for the separate and joint exposure doses are 0, 1.56, 3.12, 6.25, 12.5, 25 μg/mL, and each concentration is set in three parallel groups.

Preparing 2',7'-Dichlorodihydrofluorescein diacetate (DCFH-DA) solution: accurately weighing a 4.8729 mg DCFH-DA standard product to dissolve it in 1 ml DMSO, obtaining 10 mM DCFH-DA mother liquor and storing it at −20° C.

Referring to Example 2, collecting the nematodes after separately and jointly exposing the TeA and PAT for 48 h into a 1.5 mL EP centrifuge tube, after natural lysis, washing the nematodes 2-3 times with K-medium solution, collecting the nematodes on the bottom into a new 12-hole culture plate, enabling each hole to contain 500 μL K-medium solution and 500 μL DCFH-DA working solution (the final concentration of DCFH-DA is 50 μM), incubating at 20° C. for 2 h from light exposure, after finishing incubation, collecting the nematodes into a 1.5 mL EP centrifuge tube, washing the residual liquid with K-medium solution then removing the supernatant, adding 200 μL of 10% formalin solution for fixation, extracting the anesthetized nematodes to a glass substrate, observing and photographing it under a fluorescence upright microscope, then measuring the fluorescence intensity by means of Image J software, enabling no less than 20 nematodes to be measured in each concentration group; the data processing method is the same as Example 2. The statistics on the test results are shown in FIG. 3.

Figure 3:
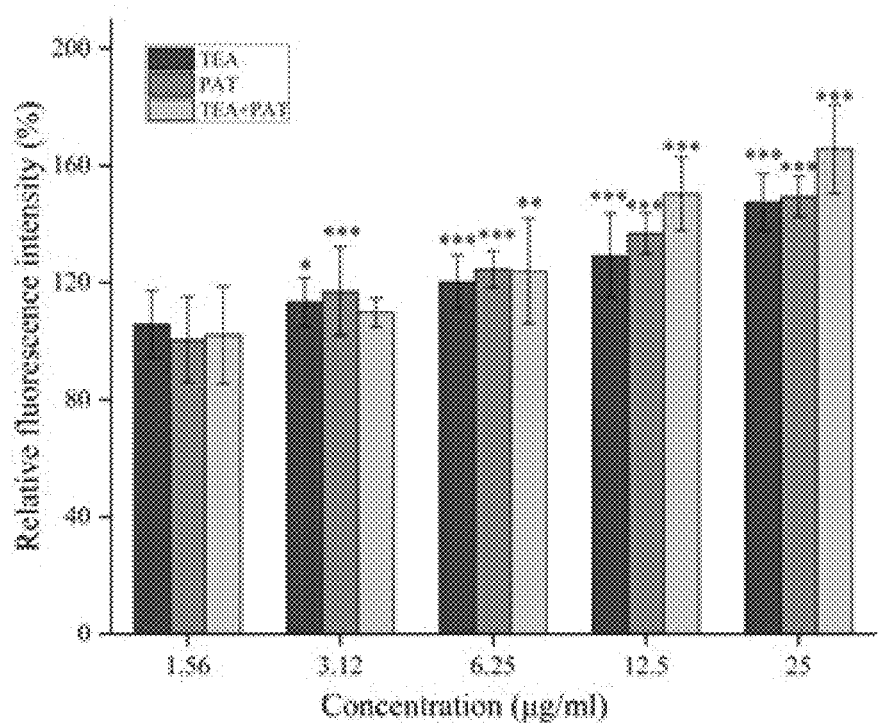

FIG. 3 shows the effects of separately and jointly exposing the TeA and PAT on oxidative stress of *Caenorhabditis elegans*. The accumulation of ROS in nematodes gradually increases with the increase of concentration, when the separate and joint concentration is 12.5 μg/mL, the relative fluorescence intensity ratios of TeA, PAT, and TeA+PAT are 129.26%, 136.92% and 150.38%, respectively; when the concentration is 25 μg/mL, the relative fluorescence intensity ratios are 147.51%, 149.43% and 165.72%, respectively. The above shows that the TeA and PAT synergistically increase ROS production in nematodes, causing a stronger oxidative stress response.

Example 5

The present example establishes a toxic biological model of mutant strains Daf-16 (mu86) and Daf-2 (e1370). By detecting the effects of separately and jointly exposing the TeA and PAT on the growth, development and reproductive ability of *Caenorhabditis elegans* and comparing that with N2 wild type, the effects of Daf-16 and Daf-2 on the joint toxicity of the TeA and PAT are evaluated. The specific steps are as follows.

Obtaining the synchronized L1-stage nematodes of Daf-16 and Daf-2 according to the method of Example 1, then detecting the effects of TeA, PAT, TeA+PAT (their exposure concentrations are the same as N2) on the growth and development and reproductive ability of mutant strains Daf-16 and Daf-2 according to Example 2 and 3.

The data processing method is the same as Example 2, * stands for a significant difference from the blank treatment group of the identical nematode strain, #stands for a significant difference from the N2 wild-type nematode.

Figure 4A:
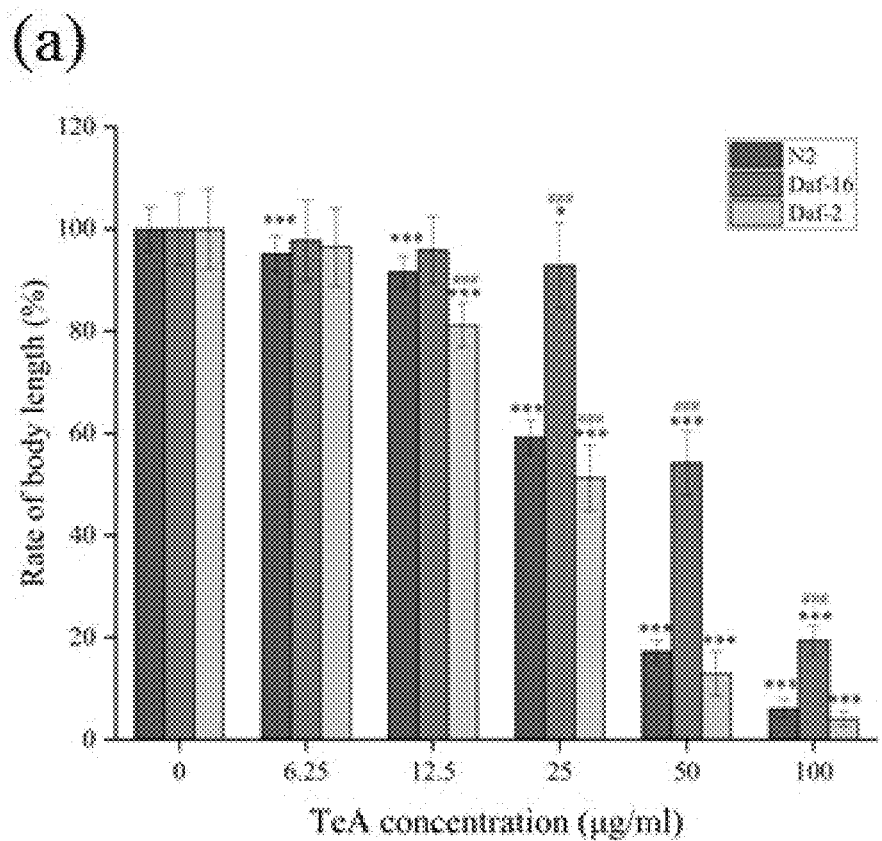
Figure 4B:
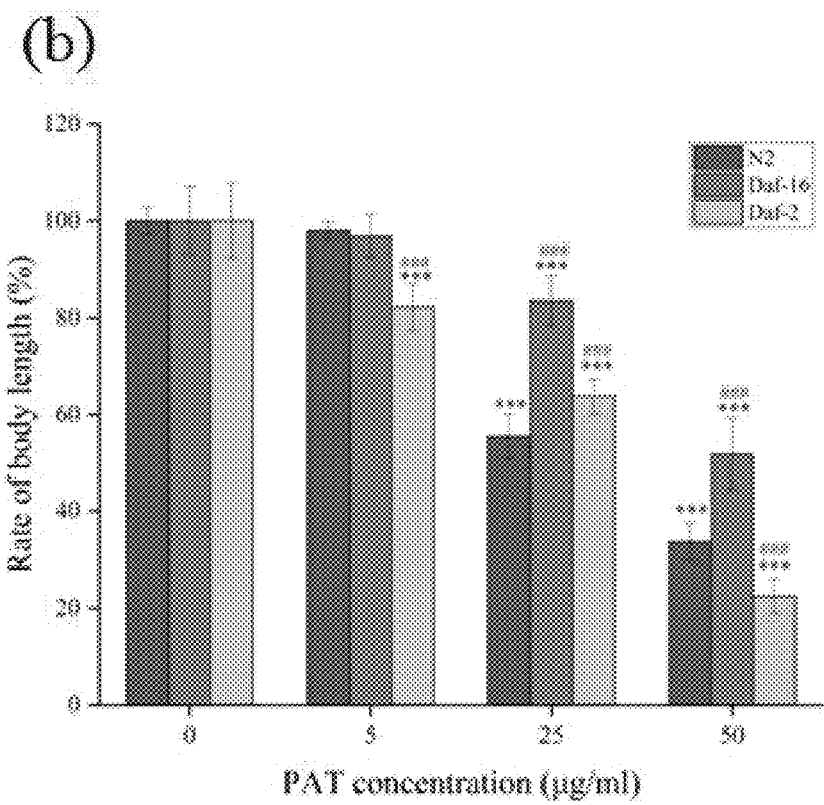
Figure 4C:
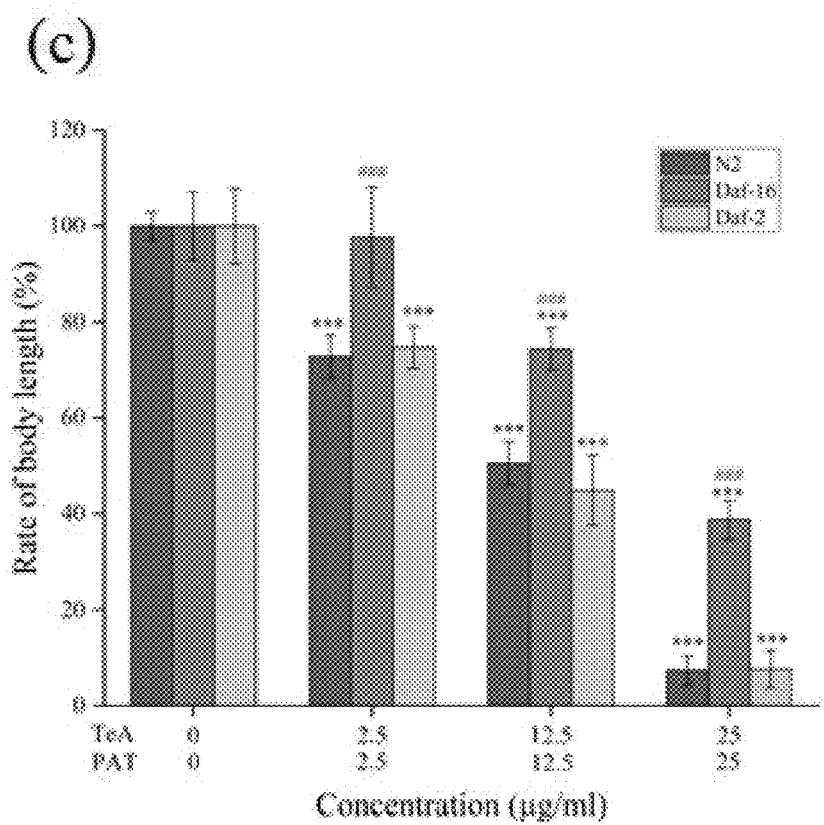
Figure 5A:
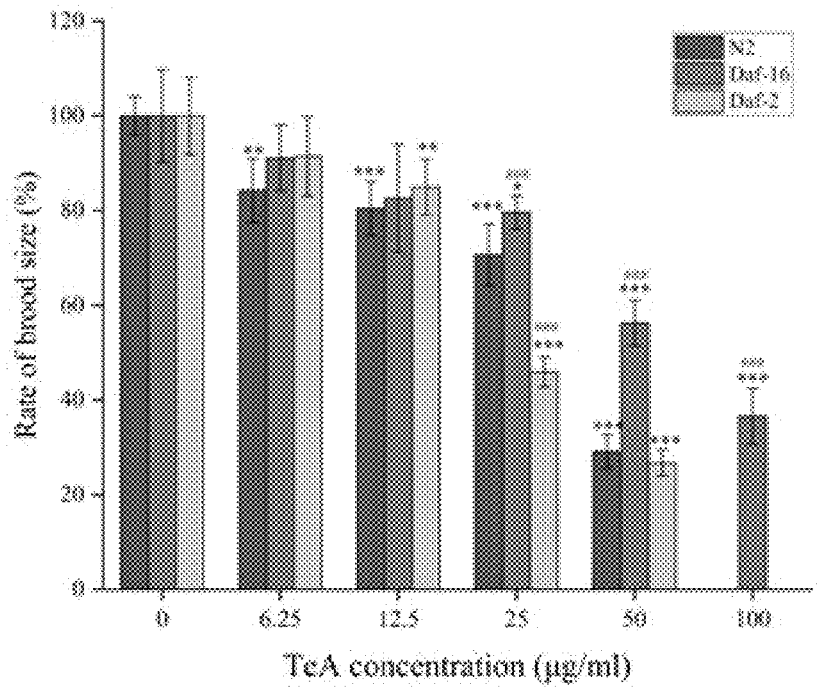
Figure 5B:
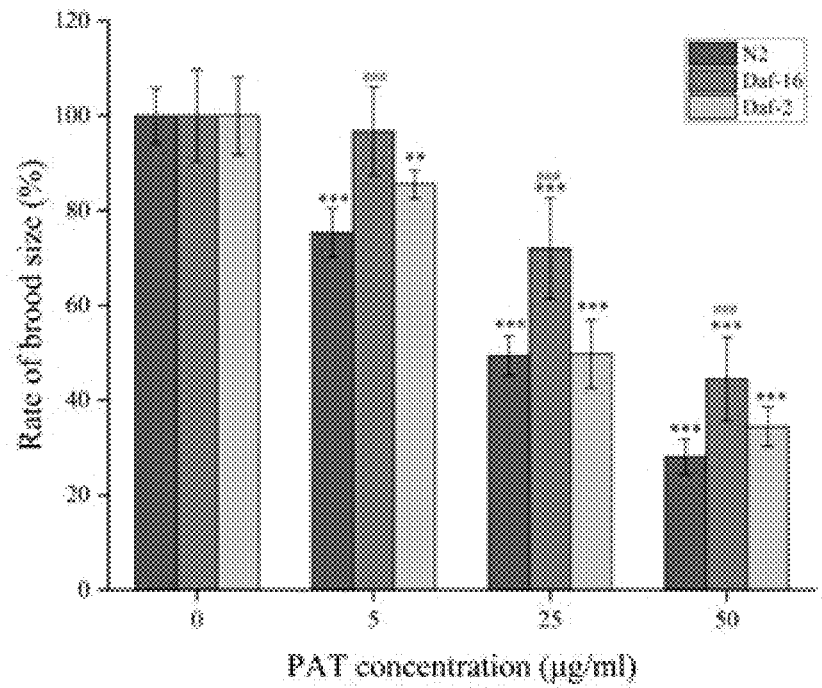
Figure 5C:
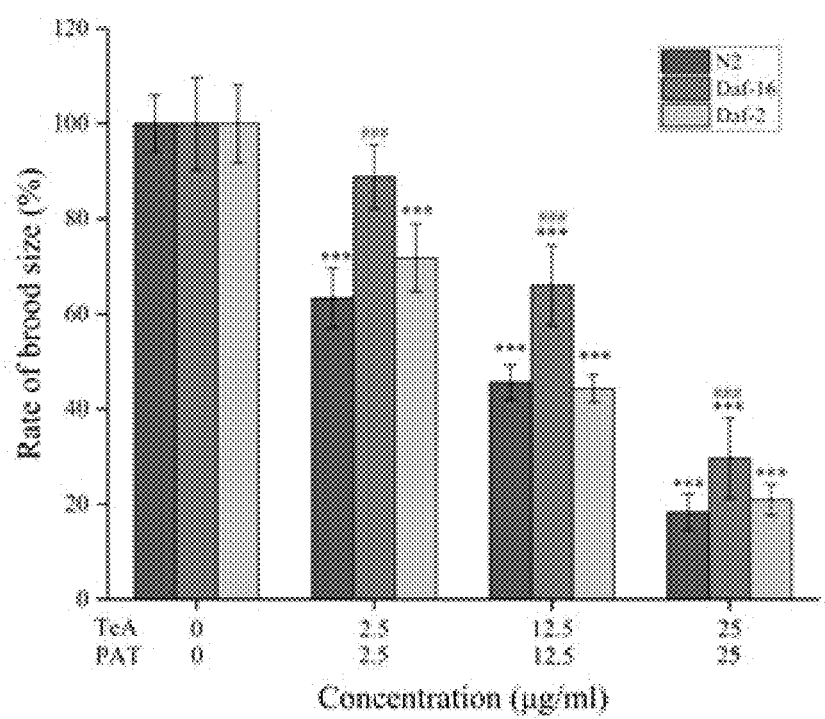

The test results are shown in FIGS. 4A-4C (showing the effects of exposing the TeA, PAT, TeA+PAT on the growth and development of nematode mutant strains, respectively) and FIGS. 5A-5C (showing the effects of exposing the TeA, PAT, TeA+PAT on the reproductive ability of nematode mutant strains).

It can be seen from FIGS. 4A-4C that the Daf-16 mutant strain has a higher body length ratio than the N2 wild type at the same concentration, and Daf-2 gene silencing does not slow down the developmental toxicity of the TeA and PAT, indicating that Daf-16 participates in regulating the TeA and PAT toxicity mechanism.

It can be seen from FIGS. 5A-5C that the Daf-16 mutant strain has a higher spawning rate than the N2 wild-type at the same concentration, but the Daf-2 mutant strain has no significant difference from N2, further indicating that the Daf-16 gene plays an important role in the TeA and PAT toxicity mechanism.

It is necessary to point out here that the above examples are only intended to further describe and explain the technical solution of the present invention, and not pose a limitation on the technical solution of the present invention, and the method of the present invention is only a preferred embodiment, not used to limit the protection scope of the present invention. Any modification, equivalent substitution, improvement and the likes made within the essence and principle of the present invention shall fall within the protection scope of the present invention.

What is claimed is:

1. A method for making a *Caenorhabditis elegans* model for assessing toxicity, comprising the steps of obtaining L1-stage *Caenorhabditis elegans*, the *Caenorhabditis elegans* being a mutant strain Daf-16 or a mutant strain Daf-2; adding the L1-stage *Caenorhabditis elegans* to a mixed system of working solution of mycotoxins containing tenuazonic acid and penicillin, K-medium solution, and E.coliOP50, the concentration ratio of the tenuazonic acid to the penicillin being 1:1, the concentration of the tenuazonic acid being at least 2.5 μg/mL, and the concentration of the penicillin being at least 2.5 g/mL; and incubating the mixed system in a biological incubator for at least 24 h to obtain a biological model of *Caenorhabditis elegans*.

2. The method for making a *Caenorhabditis elegans* model for assessing toxicity according to claim 1, wherein the *Caenorhabditis elegans* is the mutant strain Daf-16.

3. The method for making a *Caenorhabditis elegans* model for assessing toxicity according to claim 1, wherein the step of obtaining the L1-stage *Caenorhabditis elegans* includes:
   adding a predetermined amount of the K-medium solution to a NGM medium containing a large number of gestational nematodes, then scraping out nematodes and eggs with an L-shaped coating rod, then pipetting them into a centrifuge tube by a Pasteur pipette, next centrifugating them to remove a supernatant; and
   adding lysis solution to the centrifuge tube for lysis, then centrifugating them to remove the supernatant, then washing them several times with K solution, next suctioning the eggs into a perforated plate, finally incubating them in a biochemical incubator to obtain synchronized L1-stage nematodes.

4. The method for making at *Caenorhabditis elegans* model for assessing toxicity according to claim 3, wherein the lysis solution is aqueous solution containing 10 g/L NaOH and 6.5% NaClO.

5. The method for making a *Caenorhabditis elegans* model for assessing toxicity according to claim 3, wherein the method further includes the step of verifying the growth and reproductive capacity of the *Caenorhabditis elegans*, and wherein the step of verifying the growth and reproductive capacity of the *Caenorhabditis elegans* follows incubating the mixed system in a biological incubator for at least 24 h.

\* \* \* \* \*